United States Patent [19]

Roush et al.

[11] Patent Number: 5,073,564
[45] Date of Patent: Dec. 17, 1991

[54] ETHYNYLBENZOTHIOPHENE PESTICIDES

[75] Inventors: David M. Roush, Princeton, N.J.; Steven G. Davis, Dayton, Ohio; Kathryn A. Lutomski, Coram, N.Y.; Gary A. Meier, Robbinsville, N.J.; Richard B. Phillips, Palo Alto, Calif.; Susan E. Burkart, Trenton, N.J.

[73] Assignee: FMC Corporation, Philadelphia, Pa.

[21] Appl. No.: 549,516

[22] Filed: Jul. 6, 1990

[51] Int. Cl.$^5$ .............. C07D 333/54; C07D 409/16; C07D 417/16; A01N 43/18
[52] U.S. Cl. .................................. 514/365; 514/443; 548/203; 549/49; 549/58
[58] Field of Search ............... 549/49, 58; 548/203; 514/365, 443

[56]         References Cited
U.S. PATENT DOCUMENTS

| 4,788,207 | 11/1988 | Lutomski | 514/365 |
| 4,826,829 | 5/1989 | Eurkart et al. | 514/95 |
| 4,889,867 | 12/1989 | Lutomski | 514/365 |
| 4,908,357 | 3/1990 | Lutomski | 514/92 |

OTHER PUBLICATIONS

Hudson, Bioact. Mol. 1988, 7, pp. 315–338.
Hudson, Chemosphere, 1989 19(8–9) 1329-43.
Hudson, Chemosphere 1989 18 (11–12) 2317-27.
Rossi, R., Carpita, A., Lezzi, A., "Palladium-Catalyzed Syntheses of Naturally-Occurring Acetylenic Thiophene and Related Compounds", Tetrahedron, vol. 40, No. 14, pp. 2773-2779.
Derwent Accession No. 87-293811.

Primary Examiner—Robert Gerstl
Attorney, Agent, or Firm—Norman L. Craig; Robert M. Kennedy; H. Robinson Ertelt

[57]        ABSTRACT

Ethynylbenzothiophene compounds of the following formula are effective as pesticides.

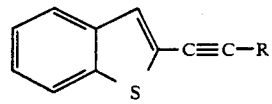

wherein R is selected from

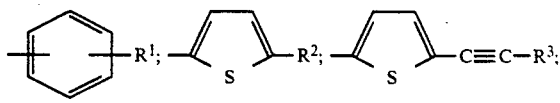

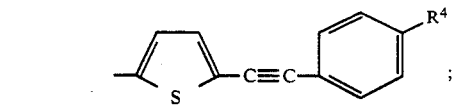

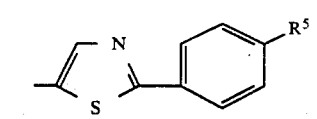

$R^1$ is selected from hydrogen, halogen, lower alkyl, lower haloalkyl, and phenylethynyl;

$R^2$ is selected from hydrogen, halogen, lower alkyl, lower alkylthio, lower haloalkenyl, haloalkenylthio, phenyl lower alkenyl, formyl, lower alkoxycarbonyl, carboxy lower alkenyl, lower alkoxycarbonyl lower alkenyl, phenyl, 2-thienyl, and methylthien-2-yl;

$R^3$ is selected from alkyl, lower trialkylsilyl, lower haloalkyl, hydroxyalkyl, alkylcarbonyl, methylthien-2-yl, 2-thienyl, and benzothien-2-yl;

$R^4$ is selected from hydrogen, halogen, lower alkyl, lower haloalkyl, lower alkoxy, lower haloalkylthio, lower alkoxycarbonyl, amino, and alkylcarbonylamino; and $R^5$ is selected from hydrogen, lower alkyl and lower haloalkyl.

21 Claims, No Drawings

ETHYNYLBENZOTHIOPHENE PESTICIDES

This invention is in the field of photoactivated pesticides. More particularly this invention concerns certain ethynylbenzothiophenes, pesticidal compositions thereof, and methods of using a broad class of such compounds to control agricultural pests.

U.S. Pat. Nos. 4,826,829 and 4,788,207 describe certain substituted ethynylthiophenes and their utility as photoactivated acaricides and insecticides. In the development of a natural product synthesis for 5-(3-buten-1-ynyl) 2,2'-bithienyl, a number of additional compounds including 2-(thien-2-ylethynyl)benzothiophene (also called 2-(2-thienylethynyl)thianaphthene) are reported to have been prepared. Bioassays of these compounds are reported to have been initiated but no results are given. See Rossi, et al., Tetrahedron, 40, 2773 (1984).

There is increasing scientific evidence that toxic reactions initiated by light play an important role in natural control of certain pest populations. In the past few years the concept of using photoactive agents as insecticides and acaricides has been advanced. Such photosensitizers typically display activity by catalyzing the conversion of ground state triplet oxygen to the excited singlet state. The excited singlet oxygen behaves as a highly active oxidizing agent, destroying the insect tissues which it contacts, hence killing the insect or acarid. The application of certain photoactive ethynylbenzothiophene compounds is thereby effective when applied to the locus where control of insects and acarids is to be maintained. The high level of photoactivated insecticidal and acaricidal activity of certain of these ethynylbenzothiophene compounds has not been previously reported.

The ethynylbenzothiophene compounds of this invention are represented by the following structural formula:

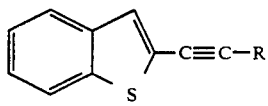

wherein R is selected from

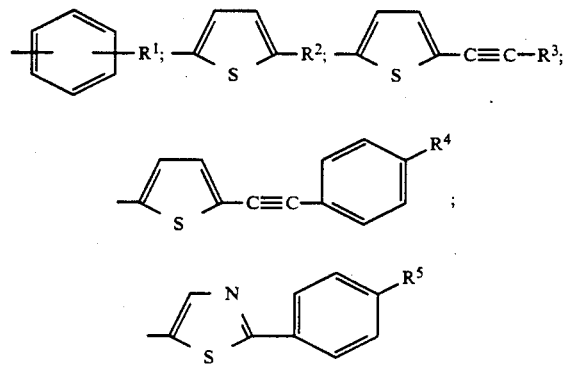

$R^1$ is selected from hydrogen, halogen, lower alkyl, lower haloalkyl, and phenylethynyl;

$R^2$ is selected from hydrogen, halogen, lower alkyl, lower alkylthio, lower haloalkenyl, haloalkenylthio, phenyl lower alkenyl, formyl, lower alkoxycarbonyl, carboxy lower alkenyl, lower alkoxycarbonyl lower alkenyl, phenyl, 2-thienyl, and methylthien-2-yl;

$R^3$ is selected from alkyl, lower trialkylsilyl, lower haloalkyl, hydroxyalkyl, alkylcarbonyl, methylthien-2-yl, 2-thienyl, and benzothien-2-yl;

$R^4$ is selected from hydrogen, halogen, lower alkyl, lower haloalkyl, lower alkoxy, lower haloalkylthio, lower alkoxycarbonyl, amino, and lower alkylcarbonylamino; and $R^5$ is selected from hydrogen, lower alkyl and lower haloalkyl.

In this description whenever the terms appear, "halo" and "halogen" mean fluorine, chlorine, bromine, and iodine. The term "lower" modifying "alkyl," "alkoxy," or the like implies a straight or branched hydrocarbon chain of 1–6 carbon atoms. "Halo" modifying "alkyl," "alkoxy," or the like means one or more hydrogen atoms have been replaced with halogen.

Among the ethynylbenzothiophene compounds encompassed by this invention, those wherein $R^2$ is other than hydrogen are new compounds. Preferred compounds of this invention are those wherein $R^4$ is chloro, methyl, isopropyl, trifluoromethyl or hydrogen.

The active compounds of this invention can be prepared by general techniques known in the art. For example, attention is directed to Takahashi, et al., Synthesis, 627 (1980); Rossi, et al., Tetrahedron, 40, 773 (1984); and Cadogan, "Organo Phosphorus Reagents in Organic Synthesis," Academic Press, New York, N.Y., 1979, p. 155. The examples which follow illustrate the methods for preparing the compounds of the invention.

EXAMPLE 1

Synthesis of 2-(Thien-2-ylethynyl)benzothiophene

Step A

2-Iodobenzothiophene

Under a nitrogen atmosphere a stirred solution of 25.0 grams (0.186 mole) of benzothiophene in 250 ml of dry tetrahydrofuran was cooled to −65° C., and 69.8 ml (0.186 mole) of n-butyllithium (2.7M in hexane) was added dropwise keeping the reaction mixture temperature below −60° C. Upon completion of addition, the reaction mixture was stirred for five minutes and then was allowed to warm to 0° C. After this time a solution of 50.8 grams (0.200 mole) of iodine in 180 ml of tetrahydrofuran was added dropwise keeping the reaction mixture temperature below 10° C. Upon completion of addition, the reaction mixture was allowed to warm to ambient temperature where it was quenched with an aqueous solution saturated with sodium metabisulfite. The reaction mixture was placed in a separatory funnel, and the organic layer was separated. The organic layer was washed with one portion of an aqueous solution saturated with sodium metabisulfite and with one portion of an aqueous solution saturated with sodium chloride. The aqueous layers were combined and washed with diethyl ether. The ether washes were combined with the organic layer, and the combination was dried with sodium sulfate. The mixture was filtered, and the filtrate was concentrated under reduced pressure to a residue. The residue was dissolved in diethyl ether and reconcentrated under reduced pressure to a residue. The residue was dissolved in warm hexane and eluted through a column of silica gel. The eluate was concentrated under reduced pressure to a volume of approximately 100 ml, and a solid crystallized from the solu-

3 tion. The mixture was cooled, and the solid was collected by filtration, yielding in two crops 18.9 grams of 2-iodobenzothiophene.

Step B

2-Trimethylsilylethynylthiophene

Under a nitrogen atmosphere a solution of 12.0 grams (0.074 mole) of 2-bromothiophene, 9.0 grams (0.092 mole) of trimethylsilylacetylene, and 120 ml of triethylamine was stirred, and 0.52 gram (catalyst) of bis(triphenylphosphine)palladium(II) chloride and 0.28 gram (catalyst) of copper(I) iodide were added. Upon completion of addition, the reaction mixture was stirred at ambient temperature during an 18 hour period. After this time the reaction mixture was concentrated under reduced pressure to a residue. The residue was dissolved in diethyl ether, and the solution was washed with two portions of an aqueous 10% ammonium chloride solution, one portion of water, and one portion of an aqueous solution saturated with sodium chloride. The organic layer was dried with sodium sulfate and filtered. The filtrate was concentrated under reduced pressure to a residue. The residue was subjected to column chromatography on silica gel. Elution was accomplished using 10% methylene chloride in hexane. The appropriate fractions were combined and concentrated under reduced pressure yielding 11.0 grams of 2-trimethylsilylethynylthiophene. The nmr spectrum was consistent with the proposed structure.

Step C

2-Ethynylthiophene

Under a nitrogen atmosphere a solution of 3.3 grams (0.018 mole) of 2-trimethylsilylethynylthiophene in 50 ml of tetrahydrofuran was stirred, and 5.8 grams (0.018 mole) of tetrabutylammonium fluoride trihydrate was added. Upon completion of addition, the reaction mixture was stirred for 30 minutes. After this time the reaction mixture was taken up in 100 ml of water and was extracted with three 75 ml portions of diethyl ether. The combined extracts were washed with three portions of water and with one portion of an aqueous solution saturated with sodium chloride. The organic layer was filtered through silica gel, and the filtrate was dried with sodium sulfate. The mixture was filtered, and the filtrate was concentrated, yielding 2.0 grams of 2-ethynylthiophene. Steps A–C were repeated several times.

Step D

2-(Thien-2-ylethynyl)benzothiophene

This compound was prepared in a manner analogous to that of Example 1, Step B, using 4.2 grams (0.016 mole) of 2-iodobenzothiophene (prepared as in Example 1, Step A), 2.2 grams (0.020 mole) of 2-ethynylthiophene (prepared as in Example 1, Step C), and catalytic amounts of bis(triphenylphosphine)palladium(II) chloride and copper(I) iodide in 50 ml of triethylamine. The yield of 2-(thien-2-ylethynyl)benzothiophene was 3.5 grams; m.p. 114°–116° C. The nmr spectrum was consistent with the proposed structure.

4

EXAMPLE 2

2-[5-(4-Trifluoromethylphenylethynyl) Thien-2-ylethynyl]benzothiophene

Step A

2-Trimethylsilylethynylbenzothiophene

This compound was prepared in a manner analogous to that of Example 1, Step B, using 40.9 grams (0.157 mole) of 2-iodobenzothiophene (prepared as in Example 1, Step A), 17.0 grams 0.173 mole) of trimethylsilylacetylene, and catalytic amounts of bis(triphenylphosphine)palladium(II) chloride and copper(I) iodide in 400 ml of triethylamine. The resulting 2-trimethylsilylethynylbenzothiophene was used in the next reaction without being isolated.

Step B

2-(Thien-2-ylethynyl)benzothiophene

The reaction mixture from Step A containing 2-trimethylsilylethynylbenzothiophene was stirred, and 4.96 grams (0.0157 mole) of tetrabutylammonium fluoride trihydrate and 10.1 grams (0.173 mole) of potassium fluoride were added. Upon completion of addition, the reaction mixture was stirred at ambient temperature for 4.5 hours. After this time 36.3 grams (0.173 mole) of 2-iodothiophene was added via syringe. Upon completion of addition, the reaction mixture was stirred at ambient temperature for 60 hours. After this time the reaction mixture was dissolved in diethyl ether and a small amount of methylene chloride, and it was washed with two portions of an aqueous solution of 10% ammonium chloride, one portion of water and one portion of an aqueous solution saturated with sodium chloride. The organic layer was dried with sodium sulfate and filtered. The filtrate was concentrated under reduced pressure to a residue. The residue was subjected to column chromatography on silica gel. Elution was accomplished with hexane and 20% methylene chloride in hexane. The appropriate fractions were combined and concentrated under reduced pressure, yielding 35.1 grams of 2-(thien-2-ylethynyl)benzothiophene.

Step C

2-(5-Iodothien-2-ylethynyl)benzothiophene

This compound was prepared in a manner analogous to that of Example 1, Step A, using 10.0 grams (0.0416 mole) of 2-(thien-2-ylethynyl)benzothiophene, 20 ml (0.050 mole) of n-butyllithium (2.5 molar in hexane) and 13.9 grams (0.0549 mole) of iodine in 100 ml of tetrahydrofuran. The yield of 2-(5-iodothien-2-ylethynyl)benzothiophene was 9.5 grams.

Step D

1-(4-Trifluoromethylphenyl)-2-trimethylsilylethyne

This compound was prepared in a manner analogous to that of Example 1, Step B, using 17.7 grams (0.0787 mole) of 4-trifluoromethylbromobenzene, 10.9 grams (0.111 mole) of trimethylsilylacetylene, 0.62 gram (0.0009 mole) of bis(triphenylphosphine)palladium(II) chloride and 0.34 gram 0.0018 mole) of copper(I) iodide in triethylamine. The yield of 1-(4-trifluoromethylphenyl)-2-trimethylsilylethyne was 19.8 grams. The nmr spectrum was consistent with the proposed structure.

Step E

4-Trifluoromethylphenylethyne

This compound was prepared in a manner analogous to that of Example 1, Step C, using 19.0 grams (0.0784 mole) of 1-(4-trifluoromethylphenyl)-2-trimethylsilylethyne and 24.7 grams (0.0784 mole) of tetrabutylammonium fluoride trihydrate in 200 ml of diethyl ether. The reaction mixture was filtered through silica gel, and the silica gel was washed with diethylether. The wash and filtrate were combined and concentrated under reduced pressure yielding, 22.9 grams of ether concentrate which was predominantly 4-trifluoromethylphenylethyne.

Step F

2-[5-(4-Trifluoromethylphenylethynyl)thien-2-ylethynyl]benzothiophene

This compound was prepared in a manner analogous to that of Example 1, Step B, using 0.5 gram (0.0014 mole) of 2-(5-iodothien-2-ylethynyl)benzothiophene (prepared as in Example 2, Step C), 0.26 gram 0.0015 mole) of 4-trifluoromethylphenylethyne (prepared in Example 2, Step E), and catalytic amounts of bis(triphenylphosphine)palladium(II) chloride and copper (I) iodide in triethylamine. The yield of 2-[5-(4-trifluoromethylphenylethynyl)thien-2-ylethynyl]benzothiophene was 0.25 gram; m.p. 149°–150° C. The nmr spectrum was consistent with the proposed structure.

EXAMPLE 3

2-(5-Methylthien-2-ylethynyl)benzothiophene

This compound was prepared in a manner analogous to that of Example 1, Step A, using 0.50 gram (0.0021 mole) of 2-(thien-2-ylethynyl)benzothiophene (prepared as in Example 2, Steps A and B), 0.33 gram (0.0023 mole) of methyl iodide, and 1.5 ml (0.0023 mole) of n-butyllithium in 10 ml of tetrahydrofuran. The yield of 2-(5-methylthien-2-ylethynyl)benzothiophene was 0.4 gram; m.p. 85°–87° C. The nmr spectrum was consistent with the proposed structure.

EXAMPLE 4

2-(5-Phenylthien-2-ylethynyl)benzothiophene

Step A

Tributyl 5-(benzothien-2-ylethynyl)thien-2-yltin

This compound was prepared in a manner analogous to that of Example 1, Step A, using 3.0 grams (0.013 mole) of 2-(thien-2-ylethynyl)benzothiophene (prepared as in Example 2, Steps A and B), 4.7 grams (0.014 mole) of tributyltin chloride and 5.5 ml (0.014 mole) of n-butyllithium (2.5M in hexanes), in 30 ml of tetrahydrofuran. The yield of tributyl 5-(benzothien-2-ylethynyl)thien-2-yltin was 1.2 grams.

Step B

2-(5-Phenylthien-2-ylethynyl)benzothiophene

To a stirred solution of 1.0 gram (0.0019 mole) of tributyl 5-(benzothien-2-ylethynyl)thien-2-yltin and 0.33 gram (0.0021 mole) of bromobenzene in 10 ml of tetrahydrofuran was added a catalytic amount of bis(triphenylphosphine)palladium(II) chloride. Upon completion of addition, the reaction mixture was warmed to reflux where it was stirred for 18 hours. After this time the reaction mixture was cooled to ambient temperature, and then it was subjected to column chromatography on silica gel. Elution was accomplished with hexane. The appropriate fractions were combined and concentrated under reduced pressure, yielding 0.28 gram of 2-(5-phenylthien-2-ylethynyl)benzothiophene; m.p. 185°–186.5° C. The nmr spectrum was consistent with the proposed structure.

EXAMPLE 5

2-(5-Formylthien-2-ylethynyl)benzothiophene

A stirred solution of 10 grams (0.042 mole) of 2-(thien-2-ylethynyl)benzothiophene (prepared as in Example 2, Steps A and B) in 100 ml of tetrahydrofuran was cooled to −70° C., and 20 ml (0.050 mole) of n-butyl lithium (2.5 molar in hexane) was added portionwise, keeping the reaction mixture below −60°C. Upon completion of addition, the reaction mixture was stirred for 45 minutes as the reaction mixture temperature returned to −70°C. After this time 3.8 grams (0.052 moles) of dimethylformamide as added. Upon completion of addition, the reaction mixture was stirred at −70°C. for 5 minutes and then was allowed to warm to ambient temperature. The reaction mixture was then quenched with an aqueous solution saturated with ammonium chloride, and washed in sequence with water and then with an aqueous solution saturated with sodium chloride. The organic layer was absorbed into 15 grams of silica gel which was in turn placed on a 2.5 cm long silica gel column. Elution was accomplished with a 1:1 hexane and ethyl acetate mixture. The eluate was concentrated under reduced pressure to a brown solid residue. The dried solid residue was suspended in hexane, and the hexane was decanted from the solid. The solid was dried, yielding 2.1 grams of 2-(5-formylthien-2-ylethynyl)benzothiophene. The nmr spectrum was consistent with the proposed structure.

EXAMPLE 6

2-[5-(4-Chlorophenylethynyl)thien-2-ylethynyl]benzothiophene

Step A

Diethyl (4-chlorophenyl)hydroxymethylphosphonate

Under a nitrogen atmosphere a solution of 20.0 grams (0.143 mole) of 4-chlorobenzaldehyde and 19.7 grams (0.142 mole) of diethyl phosphite was stirred at ambient temperature for 4 days. Gas chromatographic analysis of the reaction mixture indicated the reaction had not gone to completion. Ten ml of triethylamine was added, and the reaction mixture was stirred at ambient temperature for an additional 4 days. Gas chromatographic analysis of the reaction mixture indicated the reaction mixture still had not gone to completion. The reaction mixture was warmed to 40°–50° C. where it was stirred for 24 hours. After this time the reaction mixture was concentrated under reduced pressure, yielding 39.2 grams of diethyl (4-chlorophenyl)hydroxymethylphosphonate.

Step B

Diethyl (4-chlorophenyl)chloromethylphosphonate

A stirred solution of 38.0 grams (0.136 mole) of diethyl (4-chlorophenyl)hydroxymethylphosphonate in 250 ml of methylene chloride was cooled to 0° C., and a solution of 18.8 grams (0.158 mole) of thionyl chloride in 12 ml of methylene chloride was added via syringe. Upon completion of addition, the reaction mixture was allowed to warm to ambient temperature where it was stirred for 60 hours. After this time the reaction mixture was washed with two portions of aqueous 1N hydrochloric acid. The organic layer was filtered through silica gel. The silica gel was eluted with 1:1-hexane/ethyl acetate. The combined filtrates were concentrated under reduced pressure, yielding 40.5 grams of diethyl (4-chlorophenyl)chloromethylphosphonate. The nmr spectrum was consistent with the proposed structure.

Step C

2-[5-(4-Chlorophenylethynyl)thien-2-ylethynyl]benzothiophene

A stirred solution of 0.75 gram (0.0028 mole) of 2-(5-formylthien-2-ylethynyl)benzothiophene and 0.83 gram (0.0028 mole) of diethyl (4-chlorophenyl)chloromethylphosphonate in 10 ml of dimethylformamide was cooled to 0° C., and 0.94 gram (0.0084 mole) of potassium tert-butoxide was added. Upon completion of addition, the reaction mixture was stirred at 0° C. for 30 minutes and then was allowed to warm to ambient temperature where it was stirred for 18 hours. After this time the reaction mixture was subjected to column chromatography on silica gel. Elution was accomplished using hexane. The appropriate fractions were combined and concentrated under reduced pressure, yielding 0.20 gram of 2-[5-(4-chlorophenylethynyl)thien-2-ylethynyl]benzothiophene; m.p. 189°-191° C. The nmr spectrum was consistent with the proposed structure.

EXAMPLE 7

2-[2-(4-Trifluoromethylphenyl)thiazol-5-ylethynyl]benzothiophene

Step A

4-Trifluoromethylbenzthioamide

A solution of 70.9 grams (0.414 mole) of 4-trifluoromethylbenzonitrile and 60 ml (0.43 mole) of triethylamine in 400 ml of pyridine was stirred, and hydrogen sulfide was bubbled in as the progress of the reaction was monitored by thin layer chromatography. When the thin layer chromatographic analysis of the reaction mixture indicated that the reaction was complete, the hydrogen sulfide addition was terminated. The complete addition of the hydrogen sulfide required approximately 7 hours. Upon completion of addition, the reaction mixture was allowed to stand for 60 hours, after which time it was poured into ice/water. The resultant solid was collected by filtration and was dissolved in diethyl ether. The solution was washed in turn with one portion of water, two 150 ml portions of aqueous 10% hydrochloric acid solution and one portion of an aqueous solution saturated with sodium chloride. The organic layer was dried with sodium sulfate/magnesium carbonate and filtered. The filtrate was concentrated under reduced pressure, yielding 76.9 grams of 4-trifluoromethylbenzthioamide. The nmr spectrum was consistent with the proposed structure.

Step B 2-(4-Trifluoromethylphenyl)thiazole

A stirred solution of 5.0 grams (0.024 mole) of 4-trifluoromethylbenzthioamide, 4.4 grams (0.026 mole) of bromoacetaldehyde dimethyl acetal, and 4 drops of concentrated hydrochloric acid in 50 ml of ethanol was heated at reflux for 18 hours. After this time the reaction mixture was subjected to column chromatography on silica gel. Elution was accomplished using 20% ethyl acetate in hexane. The appropriate fractions were combined and concentrated under reduced pressure, yielding 3.3 grams of 2-(4-trifluoromethylphenyl)thiazole. The nmr spectrum was consistent with the proposed structure. The reaction was repeated several times.

Step C

5-Iodo-2-(4-trifluoromethylphenyl)thiazole

This compound was prepared in a manner analogous to that of Example 1, Step A, using 4.8 grams (0.021 mole) of 2-(4-trifluoromethylphenyl)thiazole, 12.2 ml (0.025 mole) of n-butyllithium (2.1 molar in hexane), and 7.3 grams (0.029 mole) of iodine in 98 ml of tetrahydrofuran. The yield of 5-iodo-2-(4-trifluoromethylphenyl)thiazole was 5.3 grams. The nmr spectrum was consistent with the proposed structure.

Step D

2-[2-(4-Trifluoromethylphenyl)thiazol-5-ylethynyl]benzothiophene

This compound was prepared in a manner analogous to that of Example 1, Step B, using 1.5 grams (0.04 mole) of 5-iodo-2-(4-trifluoromethylphenyl)thiazole, 0.86 gram (0.005 mole) of 2-ethynylbenzothiophene (prepared as in Example 2, Step C), and catalytic amounts of bis(triphenylphosphine)palladium(II) chloride and copper(I) iodide in 15 ml of triethylamine. The yield of 2-[2-(4-trifluoromethylphenyl)thiazol-5-ylethynyl]benzothiophene was 1.4 grams; m.p. 178°-180° C. The nmr spectrum was consistent with the proposed structure.

The following compounds were prepared using these and similar techniques.

TABLE 1a

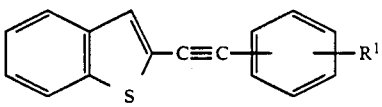

| Cmpd. No. | R¹ | M.P. (°C.) |
| --- | --- | --- |
| 1 | H | 96-100 |
| 2 | 4-Cl | 170-172 |
| 3 | 4-F | 108-110 |
| 4 | 4-CH₃ | 152-153 |
| 5 | 4-CH(CH₃)₂ | 103-104.5 |
| 6 | 2-CF₃ | 86-88 |
| 7 | 4-CF₃ | 146-147 |
| 8 | 4-C≡Cφ | 187-189 |

TABLE 1b

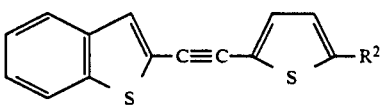

| Cmpd. No. | R² | M.P. (°C.) |
| --- | --- | --- |
| 13 | H | 114-116 |
| 14 | I | 139-141 |
| 15 | —CH₃ | 85-87 |
| 16 | —SCH₃ | 91.5-93 |
| 17 | —SCH₂CH₂CF=CF₂ | 49-50.5 |
| 18 | —CH=CF₂ | 74-76 |
| 19 | —CH=CHφ | solid |
| 20 | —CHO | 101-105 |
| 21 | —CO₂C₂H₅ | 95.5-97.5 |
| 22 | —CH=CHCO₂H | 202-203 |

TABLE 1b-continued

| Cmpd. No. | $R^2$ | M.P. (°C.) |
|---|---|---|
| 23 | —CH=CHCO$_2$CH$_3$ | 124–125 |
| 24 | phenyl | 185–186.5 |
| 25 | 2-thienyl | 158–159 |
| 26 | 5-methylthien-2-yl | 154–156 |

TABLE 1c

| Cmpd. No. | $R^3$ | M.P. (°C.) |
|---|---|---|
| 29 | —C$_3$H$_7$ | 50.5–52 |
| 30 | —C$_4$H$_9$ | liquid |
| 31 | —C$_5$H$_{11}$ | liquid |
| 32 | —C$_6$H$_{13}$ | liquid |
| 34 | —Si(CH$_3$)$_3$ | 104–106 |
| 35 | —CHFCH$_3$ | 70–72 |
| 36 | —CH(OH)CH$_3$ | 113–115 |
| 37 | —CH(OH)C$_2$H$_5$ | 75–78 |
| 38 | —CH(OH)C$_5$H$_{11}$ | 81–85 |
| 39 | —C(O)C$_2$H$_5$ | 90–92 |
| 40 | 2-thienyl | 106–108 |
| 41 | 5-methylthien-2-yl | 112–114 |
| 42 | benzothien-2-yl | 196–197.5 |

TABLE 1d

| Cmpd. No. | $R^4$ | M.P. (°C.) |
|---|---|---|
| 43 | H | 134–136 |
| 44 | Cl | 189–191 |
| 45 | F | 197–199 |
| 46 | —CH$_3$ | 178–180 |
| 47 | —CH(CH$_3$)$_2$ | 130–131.5 |
| 48 | —CH$_2$Br | solid |
| 49 | —CF$_3$ | 149–150 |
| 51 | —OC$_2$H$_5$ | 147–149 |
| 52 | —OC$_3$H$_7$ | 128.5–129.5 |
| 53 | —SCF$_3$ | 149–151 |
| 58 | —CO$_2$CH$_3$ | 169–170 |
| 59 | —NH$_2$ | 140–141 |
| 60 | —NHC(O)CH$_3$ | 223.5–225.5 |
| 61 | —NHC(O)C$_2$H$_5$ | 195–197 |
| 62 | —NHC(O)CH(CH$_3$)$_2$ | 221–224 |
| 63 | —NHC(O)C(CH$_3$)$_3$ | 192–195 |

TABLE 1e

| Cmpd. No. | $R^5$ | M.P. (°C.) |
|---|---|---|
| 64 | H | 160–166 |
| 65 | —CH$_3$ | 129–144 |
| 66 | —CF$_3$ | 178–180 |

The insecticidal and acaricidal ethynylbenzothiophene compounds of the present invention will usually not be employed free from admixture or dilution, but ordinarily will be used in a suitable formulated composition compatible with the method of application and comprising an insecticidally or acaricidally effective amount of the ethynylbenzothiophene compound. The ethynylbenzothiophene compounds of this invention, like most pesticidal agents, may be blended with agriculturally acceptable surface-active agents and carriers normally employed for facilitating the dispersion of active ingredients, recognizing the accepted fact that the formulation and mode of application of an insecticide may affect the activity of the material. The present ethynylbenzothiophene compounds may be applied, for example as sprays, dusts, or granules to the area where pest control is desired, the type of application varying of course with the pest and the environment. Thus, the ethynylbenzothiophene compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the ethynylbenzothiophene compounds. The granule particles are relatively large, a diameter of about 400–2500 microns typically. The particles are either impregnated with the ethynylbenzothiophene compound from solution or coated with the ethynylbenzothiophene compound, adhesive sometimes being employed. Granules generally contain 0.05–10%, preferably 0.5–5%, active ingredient as the insecticidally effective amount.

Dusts are admixtures of the ethynylbenzothiophene compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide or acaricide. These finely divided solids have an average particle size of less than about 50 microns. A typical dust formulation useful for controlling insects contains 1 part of the compound and 99 parts of talc.

The ethynylbenzothiophene compounds of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% of the ethynylbenzothiophene compound and 95–50% inert material, which includes surface-active dispersing, emulsifying and wetting agents, but even higher concentrations of active ingredient may be employed experimentally. The concentrates are diluted with water or other liquids for practical application as sprays, or with additional solid carrier for use as dusts.

A typical 50% wettable powder formulation would consist of 50.0% (wt/wt) of the active ingredient, 22.0% attapulgite diluent, 22.0% kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A solid concentrate formulation useful for controlling insects or acarids contains 1.5 parts each of sodium lignosulfonate and sodium laurylsulfate as wetting agents, 25 parts of active ingredient, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the alkynylbenzothiophene compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

A typical 50 gram per liter emulsifiable concentrate formulation would consist of 5.90% (wt/wt) of active ingredient; as emulsifiers: 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal or acaricidal composition.

Other useful formulations include simple solutions of the active ingredient in a solvent in which it is completely soluble at the desired concentration, such as acetone or other organic solvents.

An insecticidally or acaricidally effective amount of ethynylbenzothiophene compound in an insecticidal or acaricidal composition diluted for application is normally in the range of about 0.001% to about 8% by weight. Many variations of spraying and dusting compositions known in the art may be used by substituting the ethynylbenzothiophene compounds of this invention into compositions known or apparent in the art.

The insecticidal or acaricidal compositions of this invention may be formulated with other active ingredients, including other insecticides, nematicides, acaricides, fungicides, plant growth regulators, fertilizers, etc. In using the compositions to control insects or acarids, it is only necessary that an insecticidally or acaricidally effective amount of ethynylbenzothiophene compound be applied to the locus where control is desired. Such locus may, for example, be the insects themselves, plants upon which the insects feed, or the insect habitat. When the locus is soil, for example, soil in which agricultural crops are or will be planted, the active compound may be applied to and optionally incorporated into the soil. For most applications, an insecticidally or acaricidally effective amount will be about 50 to 750 g per hectare, preferably 150 g to 500 g per hectare.

The alkynylbenzothiophenes of the present invention were tested for insecticidal and acaricidal activity under ultraviolet light in foliar evaluations against the beet armyworm (*Spodoptera exiqua* (Hubner)), southern armyworm (*Spodoptera eridania*), Mexican bean beetle *Epilachna varivestis*), cabbage looper (*Trichoplusia ni*), tobacco budworm (*Heliothis virescens* (Fabricius)), and a phosphate susceptible strain of the twospotted spider mite (*Tetranychus urticae*). The above are referred to in activity testing results as BAW, SAW, MBB, CL, TBW and TSM-S, respectively. The insects and acarids were exposed to ultraviolet light (wave length 320–400 nanometers; 1600–2400 microwatts/$cm^2$) during a 24 or 48 hour exposure period, using test procedures adapted to the various organisms in the test. Regardless of the test procedure, foliage of whole plants or foliage removed from the whole plants was sprayed to runoff with a 10% acetone-0.25% octylphenoxypolyethoxyethanol-water solution containing up to 500 ppm of the test compound. Two replicates for each rate of application were used.

Leaves infested with adult twospotted spider mites were removed from culture plants and cut into segments each containing 50–75 female mites. Each segment was placed onto the upper leaf surface of a whole pinto bean (*Phaseolus vulgaris*) plant. After the mites had migrated to the under surfaces of the leaves, the leaf segments used to infest were removed, and each plant was sprayed with test chemical as described above. In some cases the test plants were sprayed prior to infestation with mites. After the plants had dried, the entire plant and pot were placed in metal trays in a hood and exposed to ultraviolet light at the conditions described above. A supply of water in the tray kept the plants turgid. At the end of the exposure period, the twospotted spider mites were counted with the aid of a binocular microscope at approximately 10× magnification. Each leaf was detached from the plant and placed on the microscope stage. Only live adult female mites on the underside of the leaf were counted. Moribund mites were considered dead. The condition of the test plant was noted as was any reduced feeding or phytotoxicity relative to the untreated check.

In tests utilizing the Mexican bean beetle, beet armyworm, cabbage looper, southern armyworm, and tobacco budworm, the pinto bean test plants were sprayed with test chemical and allowed to dry as previously described. Each test plant was cut off at the soil line, and the stem was pushed through a small diameter hole punched in the bottom of an eight ounce waxed container. Ten second instar larvae were counted into each container, which was covered with a glass petri dish and, with the plant stem protruding from the bottom, placed on a holding rack which allowed the stem to remain in water throughout the exposure period. During the exposure period the plants were subjected to UV light as described above. At the end of the exposure period, the containers were opened, and the numbers of dead and live insects were counted. Moribund larvae, which were disoriented or unable to crawl normally, were counted as dead. The condition of the test plant was noted as was any reduced feeding or phytotoxicity relative to the untreated check.

Test results collected at the end of 48 hour exposure periods and at application rates of 50 ppm appear in Table 2.

TABLE 2

| Cmpd. No. | BAW | CL | MBB | SAW | TBW | TSM-S |
|---|---|---|---|---|---|---|
| 1 | | 10 | | | | 99 |
| | | | | | | 100 |
| 2 | | 0 | | | | 56 |
| 3 | | 15[a] | | | | 100 |
| 4 | | 5[a] | | | | 57 |
| 5 | | 0 | | | | 78 |
| 6 | | 0 | | | | 35 |
| 7 | | 20 | 70 | | | 100 |
| | | | | | | 100 |
| 8 | 70 | 30 | | 60 | 75 | 0 |
| 13 | | 0 | 50 | | | 100 |
| | | | | | | 100 |
| 14 | | 10 | | | | 100 |
| | | | | | | 65 |
| 15 | | 0 | | | | 100 |
| 16 | | 5 | | | | 100 |
| 17 | | 5 | | | | 100 |
| 18 | | | | | | 51 |
| 21 | | 5 | | | | 51 |
| 22 | | 20 | | | | 7 |
| 23 | | 30 | | | | 27 |
| 24 | | 80 | | | | 98 |
| | | 45 | | | | |
| 25 | | 15[a] | | | | 100 |
| 26 | | 45 | | | | 100 |
| 29 | | 20 | | | | 100 |
| 30 | | 5 | | | | 60 |
| 31 | | 85 | 25 | 40 | | 100 |
| | | 50 | | | | |
| 32 | | 30 | | | | 100 |
| 35 | | 10 | | | | 100 |
| 36 | | 0 | | | | 98 |
| 37 | | 100 | | | | 61 |
| | | 35 | | | | |
| 38 | | 0 | | | | 41 |
| 39 | | 0 | | | | 67 |
| 40 | 5 | 75 | | 45 | | 100 |
| | | 90 | | | | 100 |
| 41 | | 45[a] | | | | 100 |
| 42 | | 70 | 20 | 70 | | 0 |
| | | 60 | | | | |
| 43 | 15 | 75 | 35 | 90 | 25 | 100 |
| | | 80 | | 65 | | |
| | | 40 | | | | |
| | | 45 | | | | |
| | | 50 | | | | |
| 44 | | 100 | | | | 48 |
| | | 55 | | | | |
| 45 | | 100 | | 35 | | 1 |
| | | 15 | | | | |
| 46 | | 55 | | 70 | | 27 |
| | | 10 | | | | |
| 47 | | 35 | | 80 | | 28 |
| | | 40 | | | | |
| 49 | | 95 | 25 | 75 | | 84 |
| | | 85 | | | | |
| | | 80 | | | | |
| 51 | | 30 | | | | 96 |
| 52 | | 30 | | | | 100 |
| 53 | | 50 | | | | 50 |
| 58 | | 85 | | | | 61 |
| | | 40 | | | | |
| | | 30 | | | | |
| 59 | | 20 | | | | 100 |
| 60 | | 100 | | 35 | | 0 |
| | | 75 | | | | |
| 61 | | 100 | | | | 39 |
| | | 100 | | | | |
| | | 25 | | | | |
| 62 | | 0 | | | | 0 |
| 63 | | 5 | | | | 88 |
| 64 | | | | | | 88 |
| 65 | | | | | | 100 |
| 66 | | | | | | 96 |

TABLE 2-continued

| Cmpd. No. | BAW | CL | MBB | SAW | TBW | TSM-S |
|---|---|---|---|---|---|---|
| | | | | | | 65 |

[a]100 ppm application rate

What is claimed is:

1. A pesticidal compound of the formula

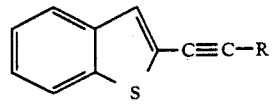

wherein R is selected from

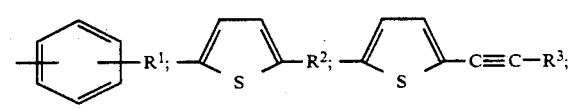

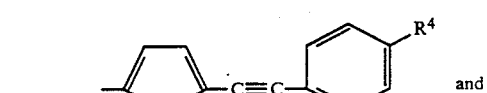

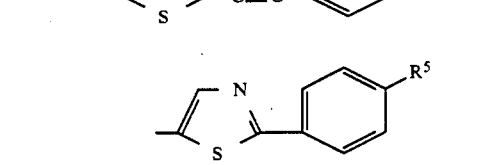

$R^1$ is selected from hydrogen, halogen, lower alkyl, lower haloalkyl, and phenylethynyl;

$R^2$ is selected from halogen, lower alkylthio, lower haloalkenyl, haloalkenylthio, phenyl lower alkenyl, formyl, lower alkoxycarbonyl, carboxy lower alkenyl, lower alkoxycarbonyl lower alkenyl, phenyl, methylthien-2-yl, and 2-thienyl;

$R^3$ is selected from alkyl, lower trialkylsilyl, lower haloalkyl, hydroxyalkyl, alkylcarbonyl, 2-thienyl, methylthien-2-yl, and benzothien-2-yl;

$R^4$ is selected from hydrogen, halogen, lower alkyl, lower haloalkyl, lower alkoxy, lower haloalkylthio, lower alkoxycarbonyl, amino, and lower alkylcarbonylamino; and $R^5$ is selected from hydrogen, lower alkyl, and lower haloalkyl.

2. A compound of claim 1 wherein R is

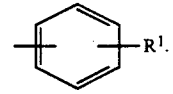

3. A compound of claim 1 wherein R is

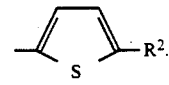

4. A compound of claim 1 wherein R is

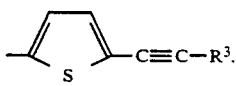

5. A compound of claim 1 wherein R is

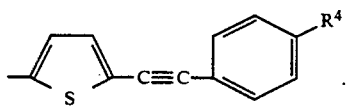

6. A compound of claim 1 wherein R is

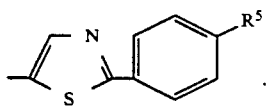

7. A compound of claim 2 wherein $R^1$ is selected from 4-C≡Cø, hydrogen, and lower haloalkyl.

8. A compound of claim 3 wherein $R^2$ is selected from halogen, methylthio, phenyl, and methylthien-2-yl.

9. A compound of claim 4 wherein $R^3$ is selected from lower alkyl, thienyl, and methylthien-2-yl.

10. A compound of claim 5 wherein $R^4$ is selected from hydrogen, chlorine, lower alkyl, and trifluoromethyl.

11. A compound of claim 6 wherein $R^5$ is methyl.

12. A compound of claim 1 wherein $R^1$ is trifluoromethyl, $R^2$ is phenyl, $R^3$ is 2-thienyl, $R^4$ is trifluoromethyl, or $R^5$ is trifluoromethyl.

13. An insecticidal or acaricidal composition comprising in admixture with an agriculturally acceptable carrier, an insecticidally or acaricidally effective amount of at least one compound of claim 1.

14. A method for controlling insects or acarids which comprises applying to the locus which experiences exposure to light where control is desired, an insecticidally or acaricidally effective amount of 50 to 750 g per hectare of at least one compound of claim 1.

15. A method for controlling insects or acarids which comprises applying to the locus which experiences exposure to light where control is desired, an insecticidally or acaricidally effective amount of 50 to 750 g per hectare of at least one compound of claim 7.

16. A method for controlling insects or acarids which comprises applying to the locus which experiences exposure to light where control is desired, an insecticidally or acaricidally effective amount of 50 to 750 g per hectare of at least one compound of claim 8.

17. A method for controlling insects or acarids which comprises applying to the locus which experiences exposure to light where control is desired, an insecticidally or acaricidally effective amount of 50 to 750 g per hectare of at least one compound of claim 9.

18. A method for controlling insects or acarids which comprises applying to the locus which experiences exposure to light where control is desired, an insecticidally or acaricidally effective amount of 50 to 750 g per hectare of at least one compound of claim 10.

19. A method for controlling insects or acarids which comprises applying to the locus which experiences exposure to light where control is desired, an insecticidally or acaricidally effective amount of 50 to 750 g per hectare of at least one compound of claim 11.

20. A method for controlling insects or acarids which comprises applying to the locus which experiences exposure to light where control is desired, an insecticidally or acaricidally effective amount of 50 to 750 g per hectare of at least one compound of claim 12.

21. A method for controlling insects or acarids which comprises applying to the locus which experiences exposure to light where control is desired, an insecticidally or acaricidally effective amount of 50 to 750 g per hectare of a compound selected from 2-(thien-2-ylethynyl)benzothiophene and 2-(5-(lower alkyl) thien-2-ylethynyl)benzothiophenes.

* * * * *